US012279843B2

(12) United States Patent
Garcia Kilroy et al.

(10) Patent No.: US 12,279,843 B2
(45) Date of Patent: *Apr. 22, 2025

(54) SURGICAL ROBOTIC SYSTEM

(71) Applicant: Verb Surgical Inc., Santa Clara, CA (US)

(72) Inventors: Pablo E. Garcia Kilroy, Santa Clara, CA (US); Karen S. Koenig, Santa Clara, CA (US); Andrea Bajo, Santa Clara, CA (US); Robert T. Wiggers, Santa Clara, CA (US); Joan Savall, Santa Clara, CA (US); Eric M. Johnson, Santa Clara, CA (US)

(73) Assignee: Verb Surgical Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/482,984

(22) Filed: Oct. 9, 2023

(65) Prior Publication Data

US 2024/0099795 A1 Mar. 28, 2024

Related U.S. Application Data

(63) Continuation of application No. 16/654,279, filed on Oct. 16, 2019, now Pat. No. 11,812,924.

(Continued)

(51) Int. Cl.
*A61B 34/37* (2016.01)
*A61B 34/00* (2016.01)
(Continued)

(52) U.S. Cl.
CPC ............. *A61B 34/37* (2016.02); *A61B 34/20* (2016.02); *A61B 34/25* (2016.02); *A61G 13/08* (2013.01);
(Continued)

(58) Field of Classification Search
CPC ......... A61B 34/30; A61B 34/32; A61B 34/35; A61B 34/37; A61B 34/70; A61B 34/20;
(Continued)

(56) References Cited

U.S. PATENT DOCUMENTS

2002/0087169 A1 7/2002 Brock et al.
2009/0036902 A1 2/2009 Dimaio et al.
(Continued)

FOREIGN PATENT DOCUMENTS

CN 105852972 A 8/2016
CN 108472097 A 8/2018
(Continued)

OTHER PUBLICATIONS

Chinese Office Action for Chinese Application No. 201811588152.2 dated Aug. 23, 2022, with English translation.
Chinese Office Action for Chinese Application No. 201811588152.2 mailed Mar. 15, 2023.
Chinese Office Action for Chinese App. No. 201811588152.2 mailed Jan. 15, 2024.

*Primary Examiner* — Aaron F Roane
(74) *Attorney, Agent, or Firm* — Lempia Summerfield Katz LLC

(57) ABSTRACT

A surgical robotic system is disclosed to include an operating table, a plurality of robotic arms and surgical instruments, a user console, and a control tower. The plurality of robotic arms are mounted on the operating table and can be stowed folded under the table for storage. The user console has one or more user interface devices, which function as master devices to control the plurality of surgical instruments.

20 Claims, 8 Drawing Sheets

Related U.S. Application Data

(60) Provisional application No. 62/754,869, filed on Nov. 2, 2018.

(51) Int. Cl.
*A61B 34/20* (2016.01)
*A61G 13/08* (2006.01)
*A61G 13/10* (2006.01)
*A61B 1/00* (2006.01)
*A61B 1/313* (2006.01)
*A61B 17/00* (2006.01)
*A61B 90/57* (2016.01)

(52) U.S. Cl.
CPC ........ *A61G 13/101* (2013.01); *A61B 1/00045* (2013.01); *A61B 1/313* (2013.01); *A61B 2017/00199* (2013.01); *A61B 2090/571* (2016.02)

(58) Field of Classification Search
CPC .............. A61B 34/25; A61B 2090/571; A61B 1/00045; A61B 1/313; A61B 2017/00199; A61G 13/08; A61G 13/06; A61G 13/04; A61G 13/02; A61G 13/101
USPC .......................................................... 606/1
See application file for complete search history.

(56) References Cited

U.S. PATENT DOCUMENTS

| | | | |
|---|---|---|---|
| 2009/0245600 A1* | 10/2009 | Hoffman | A61B 34/37 348/240.99 |
| 2009/0248036 A1 | 10/2009 | Hoffman et al. | |
| 2010/0228264 A1* | 9/2010 | Robinson | A61B 34/30 606/130 |
| 2011/0118748 A1 | 5/2011 | Itkowitz | |
| 2011/0238079 A1* | 9/2011 | Hannaford | A61B 34/76 606/130 |
| 2013/0030571 A1 | 1/2013 | Ruiz et al. | |
| 2014/0058406 A1 | 2/2014 | Tsekos | |
| 2014/0222023 A1 | 8/2014 | Kim | |
| 2016/0157942 A1 | 6/2016 | Gombert et al. | |
| 2016/0338786 A1 | 11/2016 | Robinson et al. | |
| 2017/0189127 A1* | 7/2017 | Weir | A61B 34/20 |
| 2017/0354471 A1 | 12/2017 | Farritor et al. | |
| 2018/0078034 A1 | 3/2018 | Savall et al. | |
| 2018/0078439 A1* | 3/2018 | Cagle | A61B 34/30 |

FOREIGN PATENT DOCUMENTS

| | | | |
|---|---|---|---|
| WO | 2017210500 A1 | 12/2017 | |
| WO | WO-2018007935 A1 * | 1/2018 | ............ A61B 34/00 |

* cited by examiner

SURGICAL ROBOTIC SYSTEM

CROSS-REFERENCE TO RELATED APPLICATION

This application is a continuation of U.S. application Ser. No. 16/654,279, filed Oct. 16, 2019, which claims priority claims priority to provisional U.S. Patent Application No. 62/754,869, filed Nov. 2, 2018, which is hereby incorporated by reference.

TECHNICAL FIELD

The subject technology generally relates to robotics and surgical systems, and more specifically to system architectures and components of a surgical robotic system for minimally invasive surgeries.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more surgical tools (e.g., end effectors and endoscope) through the incisions into the patient. The surgical procedures may then be performed using the introduced surgical tools, with the visualization aid provided by the endoscope.

Generally, MIS provides multiple benefits, such as reduced patient scarring, less patient pain, shorter patient recovery periods, and lower medical treatment costs associated with patient recovery. Recent technology development allows more MIS to be performed with robotic systems that include one or more robotic arms for manipulating surgical tools based on commands from a remote operator. A robotic arm may, for example, support at its distal end various devices such as surgical end effectors, imaging devices, cannulas for providing access to the patient's body cavity and organs, etc. In robotic MIS systems, it may be desirable to establish and maintain high positional accuracy for surgical instruments supported by the robotic arms.

Existing robotically-assisted surgical systems usually consist of a surgeon console that resides in the same operating room as the patient and a patient-side cart with four interactive robotic arms controlled from the console. Three of the arms hold instruments such as scalpels, scissors, or graspers, while the fourth arm supports an endoscope camera. In order to reposition the patient during a surgical procedure, surgical staff may have to undock the instruments/arms, reposition the arms/patient cart, and re-dock the instruments/arms. It may be desirable to have a surgical robotic system that allows repositioning the patient without undocking arms during general or other laparoscopic surgeries.

SUMMARY

Disclosed herein is a robotically-assisted surgical system, which is a software-controlled, electro-mechanical system, designed for surgeons to perform minimally-invasive surgery. The surgical robotic system may be comprised of three major sub-systems: a surgeon subsystem—the user console (surgeon console or surgeon bridge), a central control subsystem—the control tower, and a patient subsystem—the table and robotic arms. A surgeon seated in a surgeon seat of the user console may control the movement of compatible instruments using master user input devices (UIDs) and foot pedals. The surgeon can view a three-dimensional (3D) endoscopic image on a high-resolution open stereo display, which provides the surgeon the view of the patient anatomy and instrumentation along with icons, apps, and other user interface features. The user console may also provide an option for immersive display using a periscope, which can be pulled from the back of the surgeon seat.

The control tower can function as the control and communication center of the surgical robotic system. It may be a mobile point-of-care cart housing a touchscreen display, and include computers that control the surgeon's robotically-assisted manipulation of instruments, safety systems, a graphical user interface (GUI), an advanced light engine (also referred to as a light source), and video and graphics processors, among other supporting electronic and processing equipment. The control tower can also house third-party devices like an electrosurgical generator unit (ESU), and insufflator and $CO_2$ tanks.

The patient subsystem may be an articulated operating room (OR) table with up to four integrated robotic arms positioned over the target patient anatomy. The robotic arms of the surgical system may incorporate a remote center design, i.e., each arm pivots about a fixed point in space where the cannula passes through a patient's body wall. This reduces lateral movement of the cannula and minimizes stresses at the patient's body wall. A suite of compatible tools can be attached/detached from an instrument driver mounted to the distal end of each arm, enabling the surgeon to perform various surgical tasks. The instrument drivers can provide intracorporeal access to the surgical site, mechanical actuation of compatible tools through a sterile interface, and communication with compatible tools through a sterile interface and user touchpoints. An endoscope can be attached to any arm and provide the surgeon with the high resolution, three-dimensional view of the patient anatomy. The endoscope can also be used endoscopically (hand-held) at the start of a surgery and then be mounted on any one of the four arms. Additional accessories such as trocars (also called sleeves, seal cartridge, and obturators) and drapes may be needed to perform procedures with the surgical robotic system.

DETAILED DESCRIPTION

Examples of various aspects and variations of the subject technology are described herein and illustrated in the accompanying drawings. The following description is not intended to limit the invention to these embodiments, but rather to enable a person skilled in the art to make and use this invention.

System Overview

A robotic-assisted surgical system disclosed herein is a software-controlled, electro-mechanical system designed for surgeons to perform minimally-invasive surgery. The surgical robotic system can be used with an endoscope, compatible endoscopic instruments, and accessories. The system may be used by trained physicians in an operating room environment to assist in the accurate control of compatible endoscopic instruments during robotically-assisted urologic, gynecologic and other laparoscopic surgical procedures. The system also allows the surgical staff to reposition the patient by adjusting the table without undocking the robotic arms during urologic, gynecologic and other laparoscopic surgical procedures. The compatible endoscopic instruments and accessories for use with the surgical system are intended for endoscopic manipulation of tissue including grasping, cutting, blunt and sharp dissection, approximation, ligation, electrocautery, and suturing.

Figure 1:
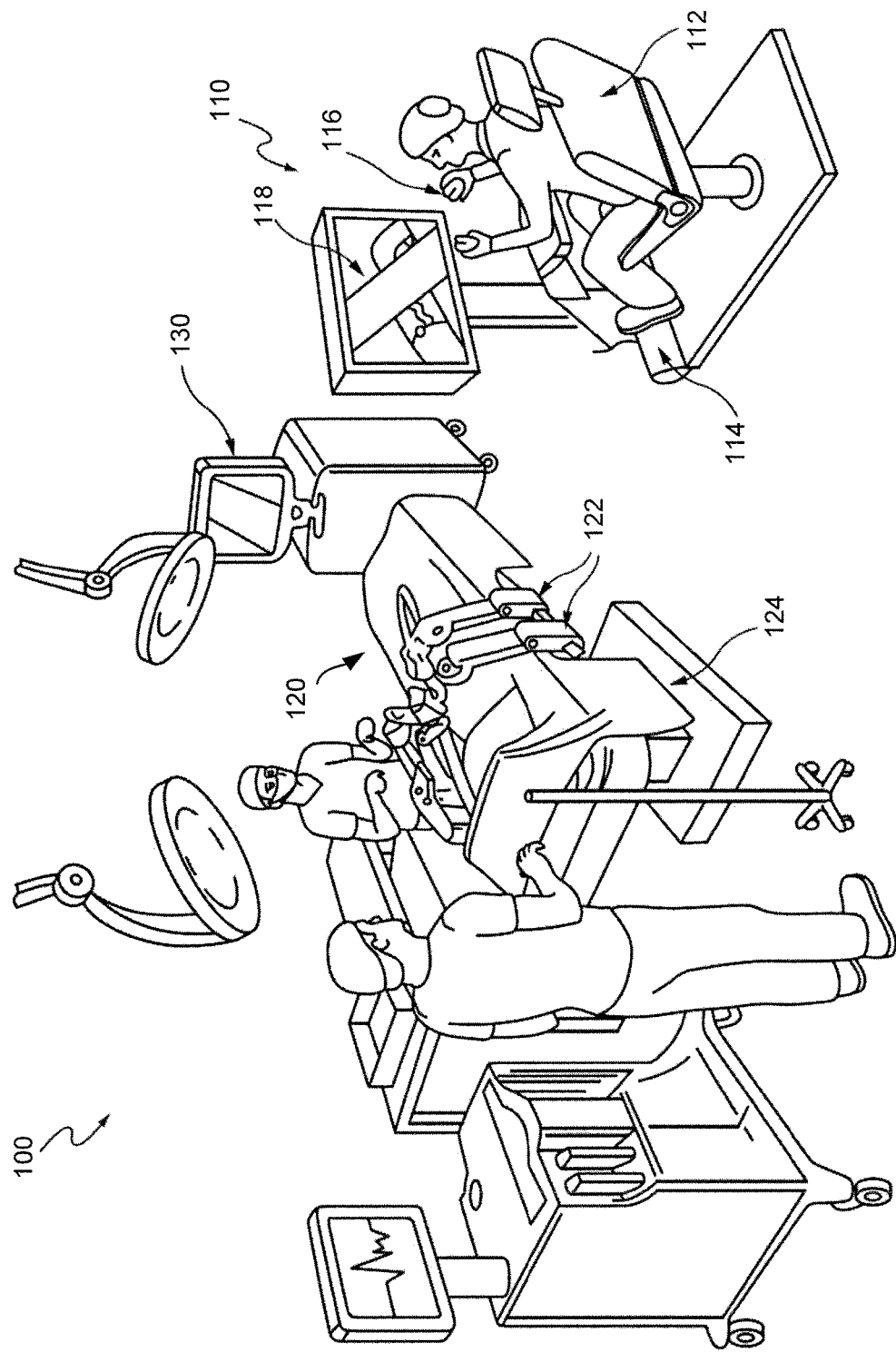
FIG. 1 is a diagram illustrating an example operating room environment with a surgical robotic system, in accordance with aspects of the subject technology.

FIG. 1 is a diagram illustrating an example operating room environment with a surgical robotic system 100, in accordance with aspects of the subject technology. As shown in FIG. 1, the surgical robotic system 100 comprises a user console 110, a control tower 130, and a surgical robot 120 having one or more surgical robotic arms 122 mounted on a surgical platform 124 (e.g., a table or a bed etc.), where surgical tools with end effectors are attached to the distal ends of the robotic arms 122 for executing a surgical procedure. The robotic arms 122 are shown as table-mounted, but in other configurations, the robotic arms may be mounted in a cart, a ceiling, a sidewall, or other suitable support surfaces.

Generally, a user, such as a surgeon or other operator, may be seated at the user console 110 to remotely manipulate the robotic arms 122 and/or surgical instruments (e.g., teleoperation). The user console 110 may be located in the same operation room as the robotic system 100, as shown in FIG. 1. In other environments, the user console 110 may be located in an adjacent or nearby room, or tele-operated from a remote location in a different building, city, or country. The user console 110 may comprise a seat 112, pedals 114, one or more handheld user interface devices (UIDs) 116, and an open display 118 configured to display, for example, a view of the surgical site inside a patient. As shown in the exemplary user console 110, a surgeon sitting in the seat 112 and viewing the open display 118 may manipulate the pedals 114 and/or handheld user interface devices 116 to remotely control the robotic arms 122 and/or surgical instruments mounted to the distal ends of the arms 122.

In some variations, a user may also operate the surgical robotic system 100 in an "over the bed" (OTB) mode, in which the user is at the patient's side and simultaneously manipulating a robotically-driven tool/end effector attached thereto (e.g., with a handheld user interface device 116 held in one hand) and a manual laparoscopic tool. For example, the user's left hand may be manipulating a handheld user interface device 116 to control a robotic surgical component, while the user's right hand may be manipulating a manual laparoscopic tool. Thus, in these variations, the user may perform both robotic-assisted MIS and manual laparoscopic surgery on a patient.

During an exemplary procedure or surgery, the patient is prepped and draped in a sterile fashion to achieve anesthesia. Initial access to the surgical site may be performed manually with the robotic system 100 in a stowed configuration or withdrawn configuration to facilitate access to the surgical site. Once the access is completed, initial positioning and/or preparation of the robotic system may be performed. During the procedure, a surgeon in the user console 110 may utilize the pedals 114 and/or user interface devices 116 to manipulate various end effectors and/or imaging systems to perform the surgery. Manual assistance may also be provided at the procedure table by sterile-gowned personnel, who may perform tasks including but not limited to, retracting tissues or performing manual repositioning or tool exchange involving one or more robotic arms 122. Non-sterile personnel may also be present to assist the surgeon at the user console 110. When the procedure or surgery is completed, the robotic system 100 and/or user console 110 may be configured or set in a state to facilitate one or more post-operative procedures, including but not limited to, robotic system 100 cleaning and/or sterilization, and/or healthcare record entry or printout, whether electronic or hard copy, such as via the user console 110.

In some aspects, the communication between the surgical robot 120 and the user console 110 may be through the control tower 130, which may translate user input from the user console 110 to robotic control commands and transmit the control commands to the surgical robot 120. The control tower 130 may also transmit status and feedback from the robot 120 back to the user console 110. The connections between the surgical robot 120, the user console 110 and the control tower 130 may be via wired and/or wireless connections, and may be proprietary and/or performed using any of a variety of data communication protocols. Any wired connections may be optionally built into the floor and/or walls or ceiling of the operating room. The surgical robotic system 100 may provide video output to one or more displays, including displays within the operating room, as well as remote displays accessible via the Internet or other networks. The video output or feed may also be encrypted to ensure privacy and all or portions of the video output may be saved to a server or electronic healthcare record system.

Prior to initiating surgery with the surgical robotic system, the surgical team can perform the preoperative setup. During the preoperative setup, the main components of the surgical robotic system (table 124 and robotic arms 122, control tower 130, and user console 110) are positioned in the operating room, connected, and powered on. The table 124 and robotic arms 122 may be in a fully-stowed configuration with the arms 122 under the table 124 for storage and/or transportation purposes. The surgical team can extend the arms from their stowed position for sterile draping. After draping, the arms 122 can be partially retracted until needed for use. A number of conventional laparoscopic steps may need to be performed including trocar placement and insufflation. For example, each sleeve can be inserted with the aid of an obturator, into a small incision and through the body wall. The sleeve and obturator allow optical entry for visualization of tissue layers during insertion to minimize risk of injury during placement. The endoscope is typically placed first to provide hand-held camera visualization for placement of other trocars. After insufflation, if required, manual instruments can be inserted through the sleeve to perform any laparoscopic steps by hand.

Next, the surgical team may positions the robotic arms 122 over the patient and attach each arm 122 to its corresponding sleeve. The surgical robotic system 100 has the capability to uniquely identify each tool (endoscope and surgical instruments) as soon as it is attached and display the tool type and arm location on the open or immersive display 118 at the user console 110 and the touchscreen display on the control tower 130. The corresponding tool functions are enabled and can be activated using the master UIDs 116 and foot pedals 114. The patient-side assistant can attach and detach the tools, as required, throughout the procedure. The surgeon seated at the user console 110 can begin to perform surgery using the tools controlled by two master UIDs 116 and foot pedals 114. The system translates the surgeon's hand, wrist, and finger movements through the master UIDs 116 into precise real-time movements of the surgical tools. Therefore, the system constantly monitors every surgical maneuver of the surgeon and pauses instrument movement if the system is unable to precisely mirror the surgeon's hand motions. In case the endoscope is moved from one arm to another during surgery, the system can adjust the master UIDs 116 for instrument alignment and continue instrument control and motion. The foot pedals 114 may be used to activate various system modes, such as endoscope control and various instrument functions including monopolar and bipolar cautery, without involving surgeon's hands removed from the master UIDs 116.

The table 124 can be repositioned intraoperatively. For safety reason, all tool tips should to be in view and under active control by the surgeon at the user console 110. Instruments that are not under active surgeon control must be removed, and the table feet must be locked. During table motion, the integrated robotic arms 122 may passively follow the table movements. Audio and visual cues can be used to guide the surgery team during table motion. Audio cues may include tones and voice prompts. Visual messaging on the displays at the user console 110 and control tower 130 can inform the surgical team of the table motion status. Arms and Table FIG. 2A is a schematic diagram illustrating one exemplary design of a robotic arm 112, a tool drive 220, and a cannula 221 loaded with a robotic surgical tool 250, in accordance with aspects of the subject technology. As shown in FIG. 2A, the example surgical robotic arm 112 may include a plurality of links (e.g., links 201-208A-B) and a plurality of actuated joint modules (e.g., joints 211-217) for actuating the plurality of links relative to one another. The joint modules may include various types, such as a pitch joint or a roll joint, which may substantially constrain the movement of the adjacent links around certain axes relative to others. Also shown in the exemplary design of FIG. 2A is a tool drive 220 attached to the distal end of the robotic arm 112. The tool drive 220 may include a cannula 221 coupled to its end to receive and guide a surgical instrument 250 (e.g., endoscopes, staplers, etc.). The surgical instrument (or "tool") 250 may include an end effector having a robotic wrist 252 and jaws 254 at the distal end of the tool. The plurality of the joint modules of the robotic arm 112 can be actuated to position and orient the tool drive 220, which actuates the robotic wrist 252 and the end effector 254 for robotic surgeries.

In some variations, the plurality of links and joints of the robotic arm 112 can be divided into two segments. The first segment (setup arm) includes links 201-205 and joints 211-215 that provide at least five degrees of freedom (DOFs). The proximal end of the first segment can be mounted to a fixture, while the distal end is coupled to the second segment. The second segment (spherical arm) includes links 206-208 providing the arm with at least two DOFs. Link 208 may comprise a first link 208A and a second link 208B operatively coupled with a pulley mechanism to form a parallelogram and to constrain the movement of the tool drive 220 around a mechanical remote center of motion (RCM). The first segment may be referred to as the setup arm because it may position and adjust the RCM in space relative to the mounting fixture, while the second segment may be referred to as the spherical arm because it is configured to move the surgical tool within a generally spherical workspace.

Figure 2B:
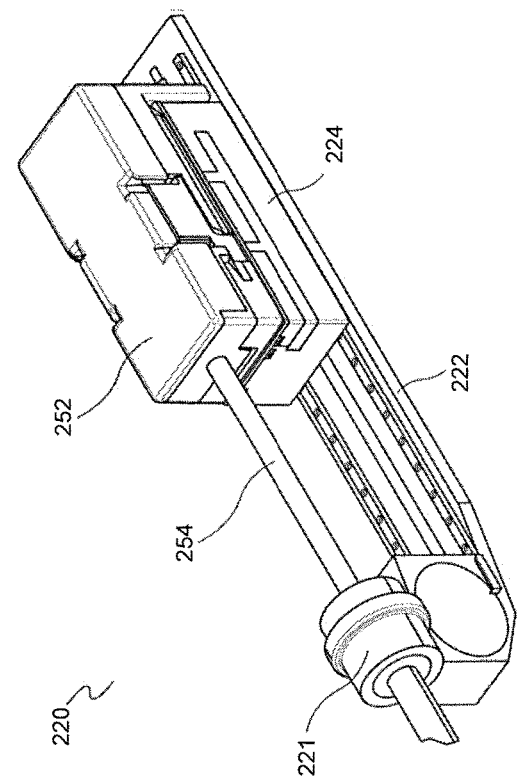
FIGS. 2B and 2C are schematic diagrams illustrating an exemplary tool drive with and without a loaded tool adjacent, respectively, in accordance with aspects of the subject technology.
Figure 2C:
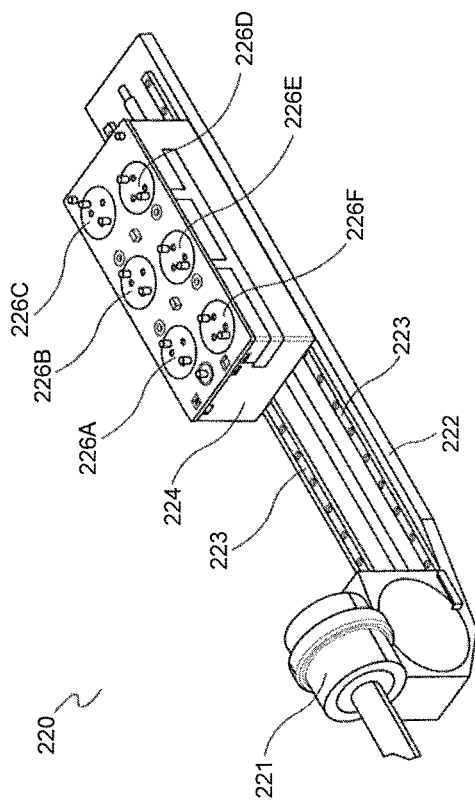
Figure 2A:
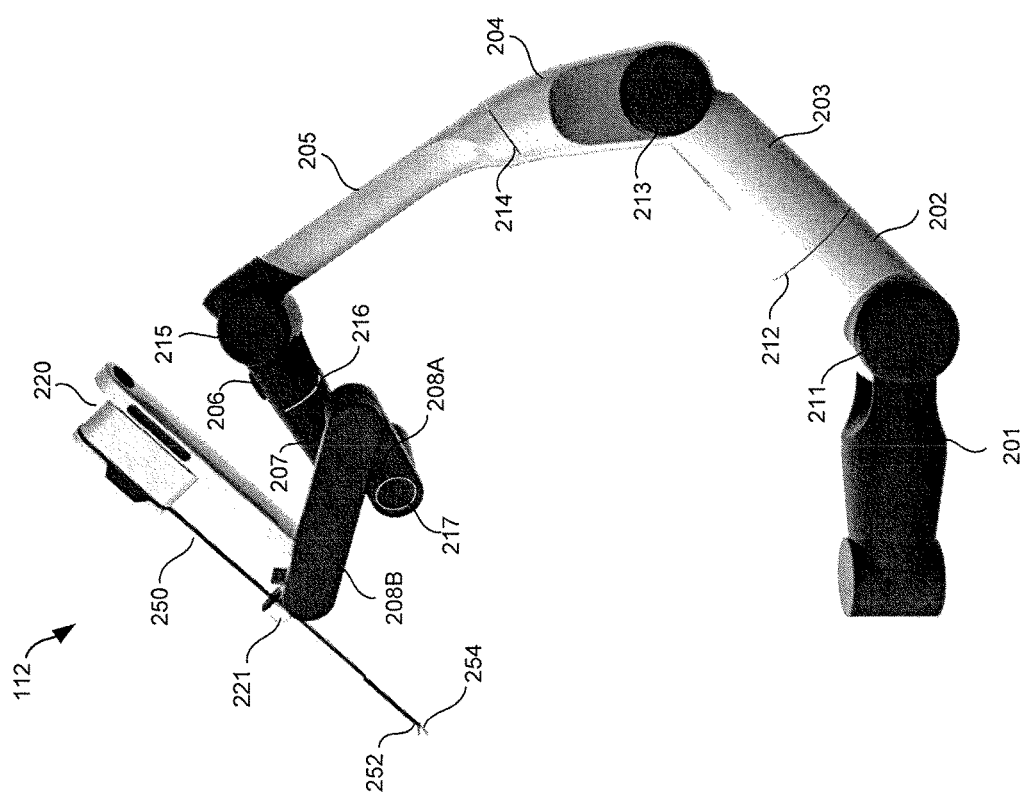
FIG. 2A is a schematic diagram illustrating one exemplary design of a robotic arm, a tool drive, and a cannula loaded with a robotic surgical tool.

FIGS. 2B and 2C are schematic diagrams illustrating an exemplary tool drive with and without a loaded tool adjacent, respectively, in accordance with aspects of the subject technology. As shown in FIG. 2B, in one variation, the tool drive 220 may include an elongated base (or "stage") 222 having longitudinal tracks 223 and a tool carriage 224, which is slidingly engaged with the longitudinal tracks 223. The stage 222 may be configured to couple to the distal end of a robotic arm such that articulation of the robotic arm positions and/or orients the tool drive 220 in space. Additionally, the tool carriage 224 may be configured to receive a tool base 252 of the tool 220, which may also include a tool shaft 254 extending from the tool base 252 and through the cannula 221, with the robotic wrist 252 and the end effector 254 (as shown in FIG. 2A) disposed at the distal end.

Additionally, the tool carriage 224 may actuate a set of articulated movements of the robotic wrist and the end effector, such as through a cable system or wires manipulated and controlled by actuated drives (the terms "cable" and "wire" are used interchangeably throughout this application). The tool carriage 224 may include different configurations of actuated drives. For example, the rotary axis drives may include a motor with a hollow rotor and a planetary gear transmission at least partially disposed within the hollow rotor. The plurality of rotary axis drives may be arranged in any suitable manner. For example, the tool carriage 224 may include six rotary drives 226A-226F arranged in two rows, extending longitudinally along the base that are slightly staggered to reduce width of the carriage and increase the compact nature of the tool drive. As clearly shown in FIG. 2C, rotary drives 226A, 226B, and 226C may be generally arranged in a first row, while rotary drives 226D, 226E, and 226F may be generally arranged in a second row that is slightly longitudinally offset from the first row.

Figure 3A:
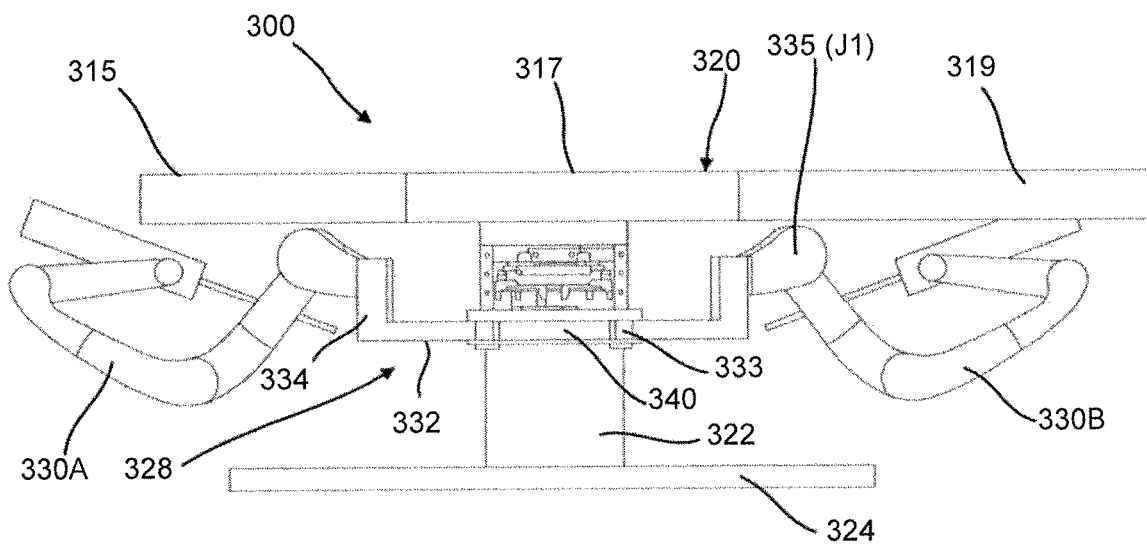
FIG. 3A is a side view of a surgical table, a table adapter, and two robotic arms coupled to the table adapter and in a stowed position.

FIG. 3A is a side view of a surgical table 300, a table adapter 328 and two robotic arms 330A-B coupled to the table adapter and in a stowed position, in accordance with aspects of the technology. As shown in FIG. 3A, a surgical table 300 includes a table top 320, a pedestal 322 (also referred to herein as support), and a base 324. The pedestal 322 can be mounted to the base 324, which can be fixed to the floor of an operating room, or can be movable relative to the floor. The table top 320 includes a head section 315, a torso section 317, and a leg section 319 along a y-axis in the longitudinal direction. The table top 320 can also include an arm section(s) (not shown). The table top 320 has a top surface on which a patient can be disposed. The pedestal 322 can provide for movement of the table top 320 in a desired number of degrees of freedom. For example, in one embodiment, the head section 316 is pivotally coupled to a first end of the torso section 317, and the leg section 319 is pivotally coupled to a second end of the torso section 317, such that the head section 316 and leg section 319 can be rotated about an x-axis extending in a lateral direction relative to the table top 320. The movement of the table top 320 and/or its constituent sections may be performed manually or driven by motors, controlled locally or remotely.

As shown in FIG. 3A, a table adapter 328 (also referred to herein as "adapter") including a table interface structure 340 is coupled to the pedestal 322 of the surgical table 300. The table interface structure 340 can be a single structure coupled to the pedestal 322 and/or the table top 320 that supports one or more robotic arms 330A-B. Via the table adapter 328, arm 330A and arm 330B may be mounted on the same side (e.g., the side shown in FIG. 3A) relative to the longitude direction of the table top 320. The adapter 328 may also include two interface mechanisms 340 coupled to the table 300 on opposite sides of the table top 320. For example, two more arms may be mounted on the other side (not shown) of the table top 320. When not in use, arm 330A (and one other arm on the opposite side not shown) may be stowed under the head section 315, while arm 330B (and another arm on the opposite side not shown) may be stowed under the leg section 319.

In some variations, the adapter 328 can be coupled to the pedestal 322, such that the adapter 328 can move vertically up and down relative to the pedestal 322. Additionally, or in alternative configurations, the table top 320 and the adapter 328 can be moved relative to each other within the plane of the table top 320. The adapter 328 may further include multiple first link members 332 that are each pivotally coupled to the table interface structure 340 at a first joint 333, and multiple second link members 334 that are each coupled to one of the first link members 332. A second link member 334 may be allowed to translate vertically relative to a corresponding first link member 332. In some variations, the second link member 334 can include a coupling portion configured to receive a mounting base of the robotic arm 330A-B. In the example shown in FIG. 3A, the coupling portion also includes the first joint 335 (J1) of the robotic arm 330B, which can be folded or collapsed under the table 300 for storage.

Figure 3B:
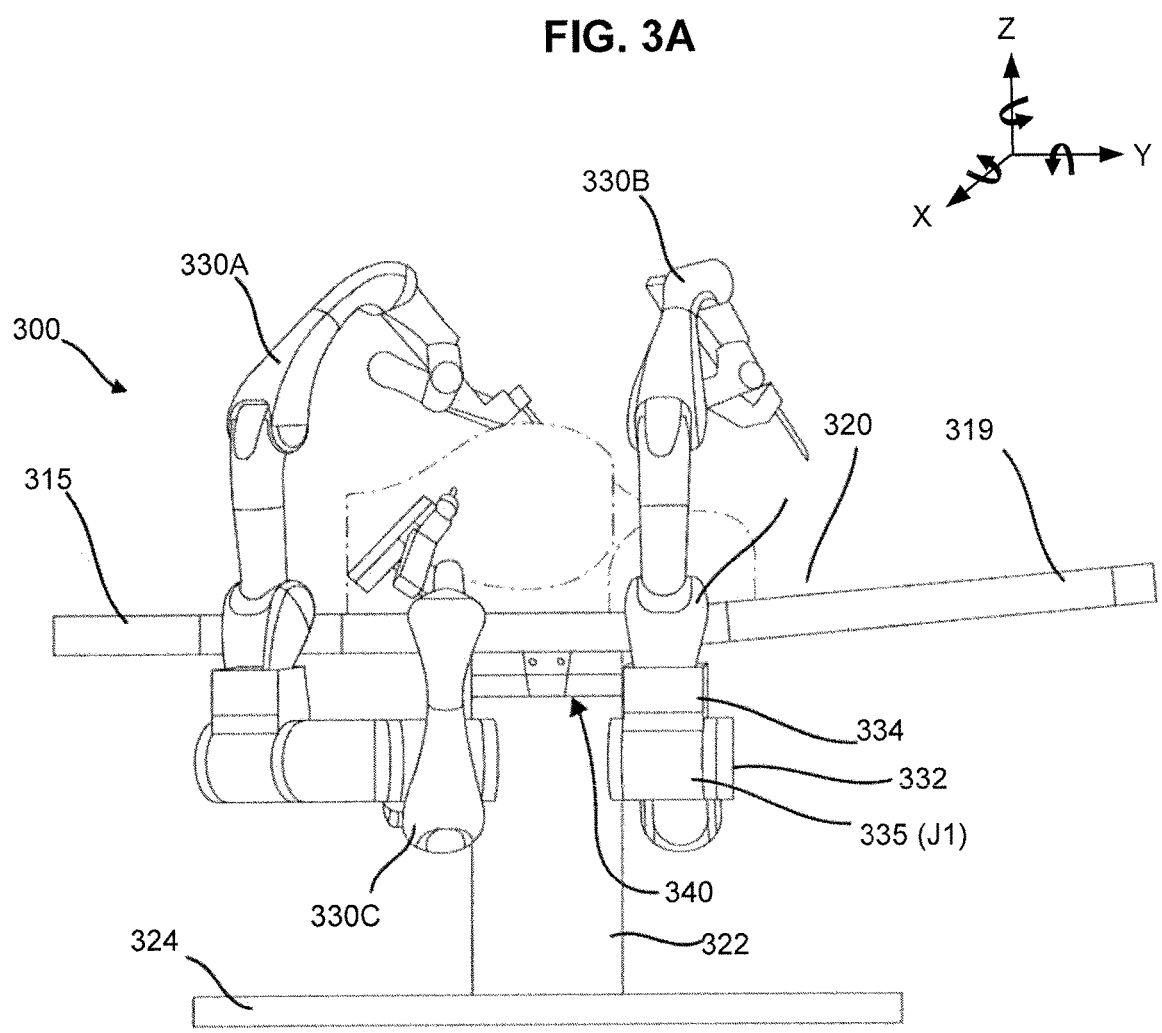
FIG. 3B is a side view of the surgical table, adapter, and arms shown in an operating position with three arms positioned on one side of the table, in accordance with aspects of the subject technology.

FIG. 3B is a side view of the surgical table 300, adapter 328, and arms 330A-C shown in an operating position with three arms 330A-C on one side of the table 300. In this example, a second joint 335 (J1) is included in the pivotal coupling between the first link member 332 and the second link member 334, so that the adapter 328 and arms 330A-C can be moved from the stowed position to various operating positions by extending the arms 330A-C via pivot joints 333 (J0) and arm joints 335 (J1). As shown in FIG. 3B, three arms 330A-C are currently positioned on the same side of the table 300. To achieve this configuration, one arm from the pair of arms coupled to the adapter 328 on one side of the table 300 (e.g., the side not shown in FIG. 3B) can be pivoted via the pivot joint 333 inwardly (e.g., coming out of paper) relative to the longitude axis of the table top 320 and extended to the other side of the table 300 (e.g., the side shown in FIG. 3B). For example, from the stowed configuration, arm 330C can be pivoted under the table top 320 (and the opposite arm 330A) across the longitude direction (i.e., y-axis) and extended upward using the second pivot joint 335 (J1) to the other side from under the table top 320. Such a configuration may be used to perform, for example, a prostatectomy procedure.

In same variations, the table 300 may be articulated in six (or fewer) degrees of freedom including translations and rotation (tilting) along X, Y, and Z axes, as shown in both FIGS. 3A and 3B. For example, the height of the pedestal 322 can be adjusted, which together with longitudinal or lateral motions (translation or rotation/tilting) of the table top 320, can allow for the table top 320 to be positioned at a desired surgical site at a certain height above the floor (e.g., to allow surgeon access) and a certain distance from the support 322. The table adapters 328 may be fixed to the bottom of the table top 320 but above any table motors (or joints) that enable the adjustments of the table top 320 along the pedestal 322. As a result, when the table top 320 is articulated, all the robotic arms 330A-C coupled to the table 300 would automatically move with the table top 320, thus maintaining relative poses (positions and orientations) during (and after) translation and rotation of the table top 320 without the need of repositioning.

User Console and UID

Figure 4A:
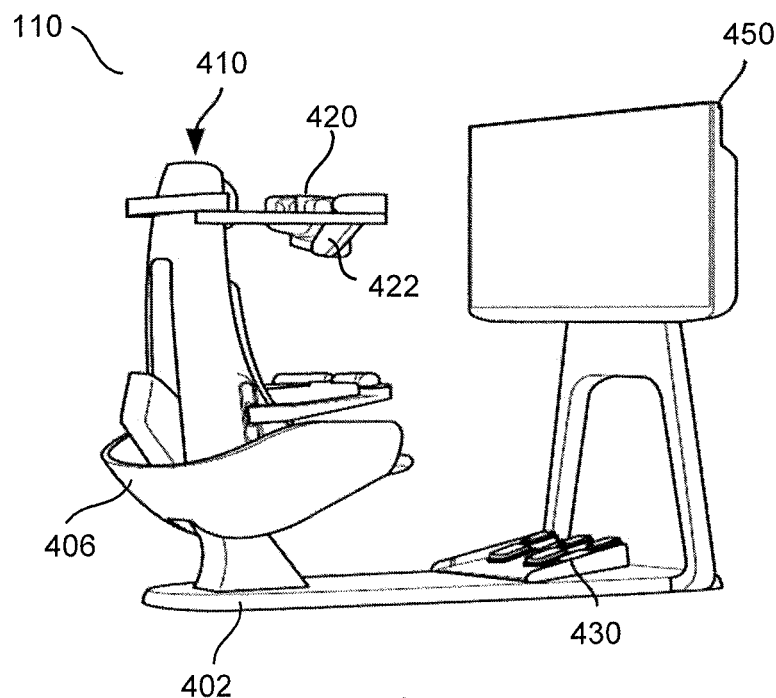
FIG. 4A is a schematic diagram illustrating a rear perspective view of an exemplary user console.
Figure 4B:
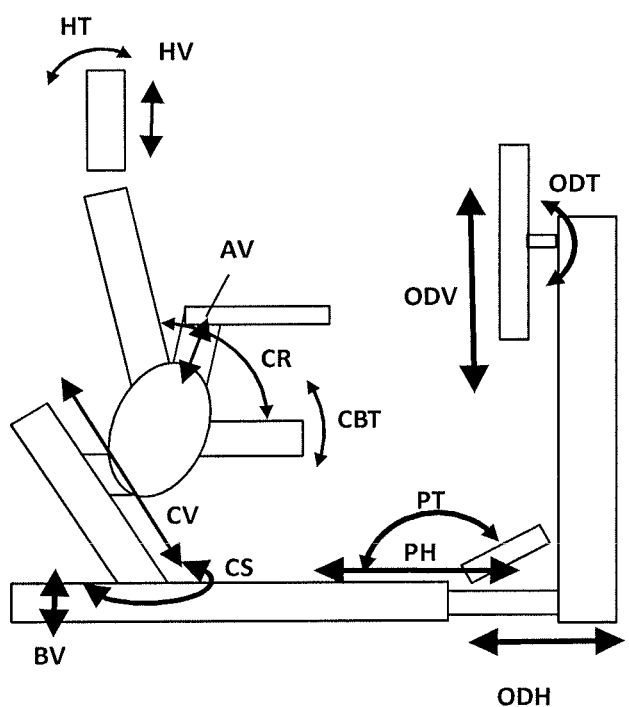
FIG. 4B is a schematic illustration of adjustable settings or parameters of the exemplary user console, in accordance with aspects of the subject technology.

Generally, as shown in FIGS. 4A and 4B, a user console 110 for remotely controlling a remote surgical robotic instrument includes a base 402, an adjustable ergonomic seat assembly 410 comprising a seat pan 406, an open display panel 450 configured to receive real-time surgical information, and a pedal assembly 430. The seat assembly 410 may be selectively configurable in a plurality of user console configurations (e.g., seated, reclined, and/or elevated). In some variations, other components of the user console 110 (e.g., display, controls, etc.) may similarly have multiple positions or configurations corresponding to the user console configurations, where the other components automatically adjust their positions or configurations in response to a selected seat assembly configuration. Furthermore, one or more of the components of the user console 110 may automatically adjust their relative positions and/or orientations according to a seating profile associated with at least one user. Exemplary variations of a user console 110 are described in further detail in U.S. patent application Ser. No. 15/712,052 titled "USER CONSOLE SYSTEM FOR ROBOTIC SURGERY" filed on Sep. 21, 2017, which is incorporated herein in its entirety by this reference.

In some variations, the user console 110 may additionally or alternatively include an immersive display, such as a periscope 420 or other head-mounted display placed in contact with the user's face or head, as shown in FIG. 4A. The immersive display 420 may be coupled to the seat assembly 410 via an immersive display support arm 422 that positions the immersive display 420 in front of the face of a user located in the seat assembly 410, such that the user may directly view content in the immersive display 410 in an immersive manner (e.g., comfortably and ergonomically immerses the user into the display environment with reduced distractions from the user's peripheral field of view). Both the open display 450 and the immersive display 420 may display various information associated with the surgical procedure (e.g., endoscopic camera view of the surgical site, static images, GUIs, etc.) and/or robotic surgical system (e.g., status, system settings), and/or other suitable information in the form of 2D and 3D video, images, text, graphical interfaces, warnings, controls, indicator lights, etc. In addition, both displays may track user's gazes, head gestures, and other head/eye movements to interact with displayed content and to control the operation of other instruments in the robotic surgical system.

To facilitate the adjustment and set-up of the user console 110 for ergonomic and other adjustments, a configuration controller may be provided that can detect and save the specific configuration of one or more components of the user console 110, including the seat assembly 410, display assembly 450, pedal assembly 430, and also control the motors of the adjustment mechanisms to restore the user console 110 to a save specific configuration. Each configuration may be linked to one or more users, user characteristics, patient or patient characteristics (e.g., height, weight), operating teams, robot system configurations, seating preferences, and/or surgery types. The configuration controller may be separate from the robot controller of the robot system, with its own processor, memory, and input/output interface to the motors, interlocks, actuators, and/or sensors, or may be part of the same system. In addition to any customized configuration, the configuration controller may include some pre-configured settings, or may include an algorithm that sets a configuration based upon the height and/or weight of the user as entered into the configuration controller, or measured by one or more sensors built into the user console (e.g., weight sensors in the seat pan 406, base 402, and/or pedal assembly 430, optical height, or length detection).

FIG. 4B illustrates an exemplary set of parameters that may, in some variations, be adjustable to configure the user console 110. The open display may be adjustable in several degrees of freedom ("DOF"). For example, open display height may be adjusted via vertical translation ("ODV") along a display support, anterior-posterior location of the open display may be adjusted via horizontal translation ("ODH") relative to a base of the user console, and open display tilt ("ODT") may be adjusted (e.g., relative to the display support). Additionally or alternatively, the pedal tray 430 may be adjustable in up to three or more DOF. For example, foot pedal tray tilt ("PT") may be adjusted (e.g., relative to the base of the user console), anterior-posterior location of the foot pedal tray may be adjusted via horizontal translation ("PH") relative to the base of the user console, and/or height of the foot pedal tray may be adjusted via vertical translation (not shown) such as with an adjustable riser coupled to the base of the user console.

The seat assembly may furthermore be adjustable in a variety of DOFs. For example, seat rotational position may be adjusted via seat swivel ("CS") around a vertical axis (e.g., by adjusting rotational swivel position of a seat support pillar as described herein), seat height ("CV") may be adjusted via translation along the seat support pillar, seat recline (generally shown as seat recline ("CR")) relative to a seat pan may be adjusted (e.g., as described in further detail herein), and seat pan tilt ("CBT") may be adjusted (e.g., as described in further detail herein). The armrest height ("AV") and other arm rest configurations (e.g., lateral or planar motion, as described further herein) may be adjusted. Additionally, headrest height ("HV") and/or headrest tilt ("HT") may be adjusted (e.g., as further described herein). Furthermore, height of the base ("By") relative to the ground may be adjusted, for example, as the result of deployment of wheels (as further described below) for transport and other suitable purposes.

In use, the user console 110 may be adjusted to a desired configuration, including ergonomic adjustments to the seat assembly 410, pedal assembly 430, and display assembly 450, but also customizations to the user interface and user interface devices, if available. The complete or a subset of the configuration may then be saved, and optionally linked to one identifier or category. The identifiers may be a user identifier, a non-user identifier category or characteristic, (e.g., surgery type, seating arrangement, etc.) and/or a biometric identifier (e.g., iris code, fingerprint, etc.). In subsequent usage, one or more identifiers are entered, provided, or selected simultaneously or serially, to narrow down the saved configuration(s) for final selection or confirmation. The configuration controller then signals or controls the various motors to make any mechanical adjustments to the user console 110, and also reconfigures or sets the configuration of the user interface. This can occur while the user is seated in the user console 110 or prior to seating, in order to reduce set-up time for a single user, or between multiple users who use the same user console 110 in respective customized configurations during a single procedure, etc. Furthermore, in some variations, the user console 110 may dynamically improve ergonomics by tracking motions of the user (e.g., body position, eye position, eye gaze, etc.) and, in response to the user's motions, automatically recommending or transitioning to an optimum configuration for the user's ergonomic, viewing, hardware, and/or other needs, such as for reducing fatigue or injury. For example, if the configuration controller detects that the user in the seat assembly 410 begins to strain upwards (as if trying to obtain a higher perspective of the operating table), the controller may automatically adjust the seat assembly 210 to elevate the user.

The plurality of user console configurations may include seated, reclined, and elevated configurations. In a seated configuration, the seat pan 406 may be at a height wherein the user's heels are in contact with or generally about the base 402 while the seat pan 406 and the user's thighs are generally aligned. The pedal assembly 430 is positioned at an anterior-posterior position wherein the user's forefoot is in contact with the pedals 430 and angled about perpendicularly to the user's lower leg. In an elevated configuration, the seat pan 406 can be elevated relative to the position in the seated configuration. The height of the seat pan 406 may be set such that the heel of the user is in contact with the base 402, but in other variations may be configured such that the user's heels are above and not in contact with the base 402. In a reclined configuration, the seat pan 406 is in a retroverted orientation along with the display panel 450.

The user interface at the user console for controlling a surgical robotic system may also include one or more handheld user interface devices (UIDs) mounted on the armrest of the seat assembly or below the open display, among other possible locations. In some variations, a user interface device held in the left hand of the user may be configured to control an end effector represented on a left side of a camera view provided to the user, while a user interface device held in the right hand of the user may be configured to control an end effector represented on a right side of the camera view. The control inputs to the user interface device may, for example, be provided by the user as input commands during the course of providing a diagnostic, surgical, laparoscopic, or minimally-invasive surgical procedure, or other robotic procedure. Exemplary variations of a user interface device are described in further detail in U.S. patent application Ser. No. 15/836,420 titled "USER INTERFACE DEVICES FOR USE IN ROBOTIC SURGERY" filed on Dec. 8, 2017, which is incorporated herein in its entirety by this reference.

In some variations, the handheld user interface device may be a groundless or ungrounded user input device configured to be held in the hand and manipulated in free space. For example, the user interface device may be configured to be held between the fingers of a user and moved about freely (e.g., translated, rotated, tilted, etc.) by the user as the user moves his or her arms, hands, and/or fingers. Additionally or alternatively, the handheld user interface device may be a body-grounded user interface device, in that the user interface device may be coupled to a portion of the user (e.g., to fingers, hand, and/or arms of a user) directly or via any suitable mechanism such as a glove, hand strap, sleeve, etc. Such a body-grounded user interface device may still enable the user to manipulate the user interface device in free space. Accordingly, in variations in which the user interface device is groundless or body-grounded (as opposed to permanently mounted or grounded to a fixed console or the like), the user interface device may be ergonomic and provide dexterous control, such as by enabling the user to control the user interface device with natural body movements unencumbered by the fixed nature of a grounded system.

FIGS. 5A-5D are illustrations of various designs for a handheld user interface device (UID) 116, in accordance with aspects of the subject technology. The UID 116 may include a housing 520 and one or more circumferential or partially-circumferential lips (or raised rings) 525. In the wired variations shown in FIGS. 5A and 5C, the UID 116 also includes a wire 550 coupling the UID 116 to the user console. In some variations, the housing 520 may have a lumen or other internal volume configured to receive electronics and/or other components. For example, the internal volume may include at least one printed circuit board (PCB) and a battery for powering the PCB and other electrical components in the UID 116. Furthermore, one or more sensors, such as accelerometers, gyroscopes, magnetometers, and/or other optical, magnetic, or capacitive sensors (not shown) can be disposed inside or on an outer surface of the housing 520 for tracking positions and orientations of the UID 116 in six degree of freedom. The UID 116 may further include one or more gesture detection sensors, for example, a proximity sensor or a grip or squeeze sensor configured to detect deformation of the housing 520, where the detected deformation of the housing 520 may be mapped to a control of the graphic user interface or the robotic system.

Figure 5A:
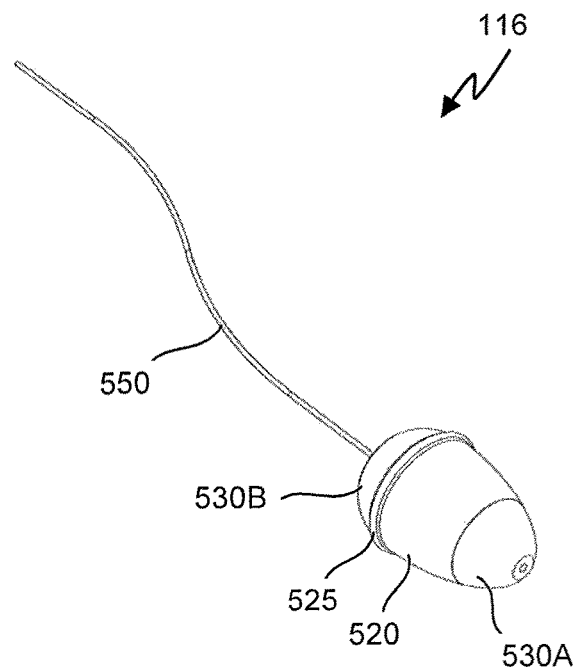
FIG. 5A is an illustrative schematic of a variation of a wired handheld user interface device in an egg shape.
Figure 5B:
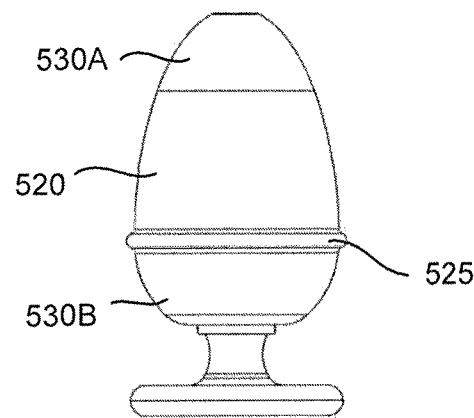
FIG. 5B is an illustrative schematic of a variation of a wireless handheld user interface device with modular and interchangeable adapters.
Figure 5C:
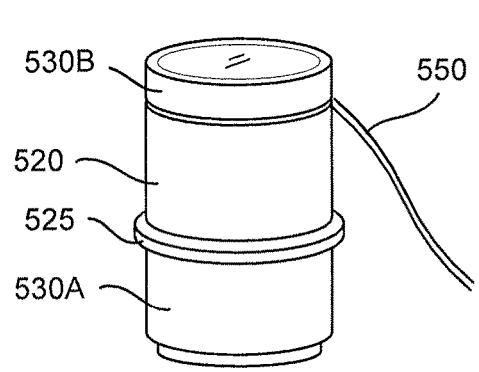
FIG. 5C is an illustrative schematic of a variation of a wired handheld user interface device in a cylinder shape.
Figure 5D:
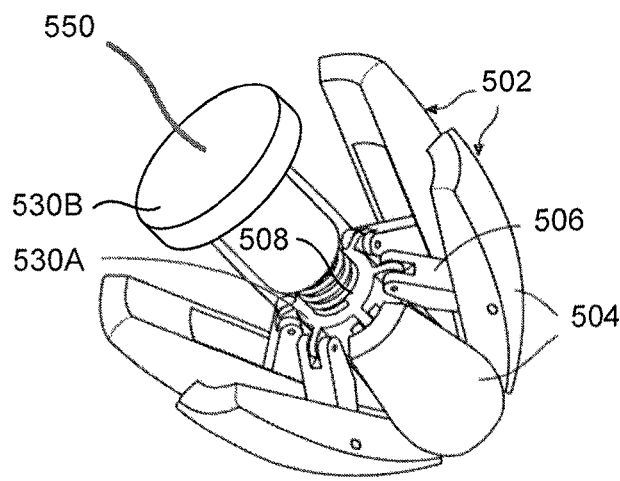
FIG. 5D is an illustrative schematic of a variation of a handheld user interface device with grip linkages, in accordance with aspects of the subject technology.

In some variations, as shown in FIGS. 5A-5D, the housing 520 of the UID 116 may have a first end 530A (e.g., proximal end) and a second end 530B (e.g., distal end), where the first end 530A and/or the second end 530B includes an engagement feature configured to couple to a detachable adapter. The detachable adapter may be interchangeable with other kinds of detachable adapters, thereby facilitating a modular design permitting multiple configurations of user interface devices, such as with different form factors, different functional features, and/or different tracking technologies in various combinations. For example, FIG. 5B depicts a disk adapter 530B that can be removably engaged onto the housing 520 and function as a joystick. In FIG. 5C, a camera adapter 530B can be mounted on the distal end of the UID 116 for optical tracking with the wire 550 coupled to the side of the UID housing 520. As another example, FIG. 5D shows another variation of the UID 116 that include a proximal end 530A coupled to or integrated with a flower-shaped grip linkage. The grip linkage may have a plurality of grip components 502, each includes a grip crank 504 and a follower arm 506 pivotally coupled to the grip crank 504. When a user presses one or more of the grip crank 504, the follower arms 506 push a slider 508 upwardly, which may trigger a sensor at the proximal end 530A to generate a grip signal for controlling jaws of the corresponding end effectors.

User console 110 may include a tracking system to track the positions and orientations of UID 116. In some variations, the tracking system may use optical tracking, in which cameras may be mounted in front of the user to capture continuous images of the UID movement. One or more markers can be printed or mounted on the UID 116 so that images can be processed to detect positions and orientations of the UID 116. The markers may be detectable in an image to determine a position or orientation of UID 116. In other variations, the camera can be mounted on the UID 116. Alternatively or in addition, the tracking system may be based on electromagnetic tracking subsystem having an electromagnetic source. Magnetic tracking can determine the position/orientation of moveable sensors relative to a fixed transmitter within a defined operating space. The sensors precisely measure the magnetic field from a transmitter, which is configured to generate a known set of field patterns. The transmitted patterns are arranged such that the system can resolve a unique spatial position and orientation from the values measured by each sensor. For example, the user console 110 may have a field generator to generate a position-varying magnetic field to establish a coordinate space in front of the user, while the UID 116 may include one or more tracking sensors capable of measuring six degrees of freedom within the coordinate space. The tracking sensors may include coils that respond to the electromagnetic field, e.g., inducing current. By measuring the coil current, a position and orientation of the tracking sensor and the UID 116 can be determined.

The tracked spatial state information can then be forwarded by the user console 110 to the control tower 130 as user input for robotic control. A control computer at the control tower 130 can process the user input to generate control commands so that end effectors of the surgical instrument or tool closely follow the tracked movements of the UID 116, which includes translations and rotations along all three axes, i.e., 6 DOF, in space. In addition to the spatial state, other gestures such as a squeeze or grip may also be tracked by one or more sensors, which can be a proximity sensor detecting deformation or mechanical linkages being pressed by user fingers. Once detected, the UID 116 may generate a grip signal and transmit the grip signal to the user console. The signals can be input to the control tower 130 for generating tool control commands such as grasping. For example, a grip signal may be translated into a tool control command to close the jaws of a grasper, while a release signal may be mapped to an open jaw command. Furthermore, the grip signal may command the surgical tool to apply grip force on tissues or surgical devices.

The UID 116 may further include a finger clutch, such as touch sensors or mechanical switches, to temporarily clutch the surgical robot. When clutched, the surgical robot 120 may pause the movement of one or more of the tool or arm actuators in response to the clutch signal. The teleoperation can be put on hold regardless of any UID movements, i.e., spatial state and/or grip signals are ignored by the system. During the clutch period, the user can reposition the UIDs 116, for example, to the center of the tracking field, without causing unwanted movement of surgical robot or surgical tools. Similarly, the user may squeeze (or release) the UID housing 520 without changing the jaw angle or gripping force of a grasper.

The user console 110 may further include sensors for tracking user eyes and/or head. In some variations, the eye tracking sensors may comprise cameras that take high frame rate images of user's eyes, projectors that create a pattern of near-infrared light on user's eyes, and image processing algorithms to analyze details of the user head or eyes and reflection patterns and to determine user's head position and gaze point. The eye (or head) trackers can be mounted on the top or bottom of the open display 450, among other proper locations in front of the seat assembly 410 facing the user. In order to calibrate the eye (or head) trackers, spatial state information of the UID 116 and the surgical robot can be leveraged. For example, while the user is using the UIDs 116 to manipulate an end effector of a surgical tool, a position of the end effector on the open display 450 can be derived as a reference gaze point based on robot joint state and mapping between reference frames of the endoscope and the display 450. The tracker can then be calibrated by comparing the reference gaze point and the tracked gaze point.

Tracking user's gaze point and/or head positions allow many applications for robotic surgeries. For example, tracking user's head position may help determine a spatial relationship between the head and the open display that impacts 3D perception. The user console computer may automatically adjust seat and monitor position and tilt so that the user's eyes are centered in front of the 3D display at a pre-determined distance for best 3D perception. Furthermore, user's gaze can be used an indication of the user's engagement in teleoperation. For instance, gaze point on the display can be used to automatically adjust the surgical area shown on the screen and/or endoscope position so that the focus of the user is at the center of the monitor where 3D perception is the best. Gaze can be used to activate apps on a side panel if the user shift focus on the side panel. As another example, when it is detected that a user's gaze stays outside the open display over a period of time, i.e., the user is not observing the surgical site for some time, the surgical robot can be paused or locked for patient's safety.

Graphic User Interface

Some exemplary aspects of a GUI for a robotic surgical system are described herein. More variations of the exemplary GUI and integrated apps are described in detail in U.S. patent application Ser. No. 15/842,485 titled "MULTI-PANEL GRAPHICAL USER INTERFACE FOR A ROBOTIC SURGICAL SYSTEM" filed Dec. 14, 2017, which is incorporated herein in its entirety by this reference. In some variations, the GUI may be displayed in a multi-panel display at a user console that controls the robotic surgical system. Additionally or alternatively, the GUI may be displayed at one or more additional displays, such as at a control tower for the robotic surgical system, at a patient bedside, etc. Another example of a display on which the GUI may be present is an immersive display such as those described in U.S. patent application Ser. No. 15/724,185 titled "IMMERSIVE THREE-DIMENSIONAL DISPLAY FOR ROBOTIC SURGERY" filed Oct. 3, 2017, which is incorporated herein in its entirety by this reference.

Generally, the GUI for a robotic surgical system may provide informative and/or interactive content, to thereby assist a user in performing a surgical procedure with one or more robotic instruments in the robotic surgical system. In some variations, the GUI may include a multi-panel display (or on multiple adjacent displays) on which content provided by various software apps may be overlaid or displayed proximate an image of the surgical site (e.g., from an endoscopic camera), such as during a surgical procedure. The software apps may be selectively arranged on the multiple panels to display their respective content in a reconfigurable manner. Different layouts of the reconfigurable panels may result from adjusting sizes and/or shapes of different panels. Additionally or alternatively, different layouts may result from the population of different content (e.g., different apps) in the multiple display panels. In some variations, a GUI may further display one or more tool widgets configured to communicate information regarding surgical instruments in a convenient, efficient manner. For example, tool widgets may summarize high-priority information such as tool type, tool state, tool settings, and/or tool "lives" remaining (e.g., number of firings left in a cartridge, etc.). Tool widgets may be overlaid over an endoscopic image, adjacent or proximate the endoscopic image, and/or or in any other suitable portion of the displayed GUI.

Figure 6A:
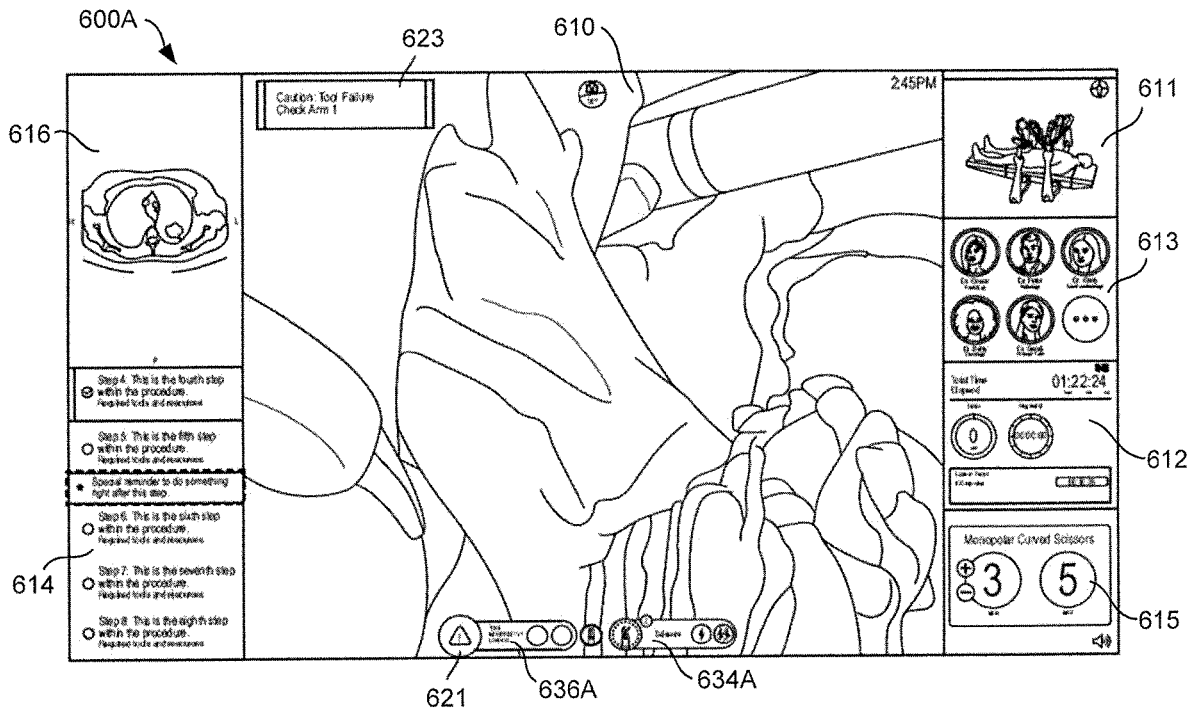
FIG. 6A is a screenshot illustrating an exemplary variation of a GUI with tool notifications.
Figure 6B:
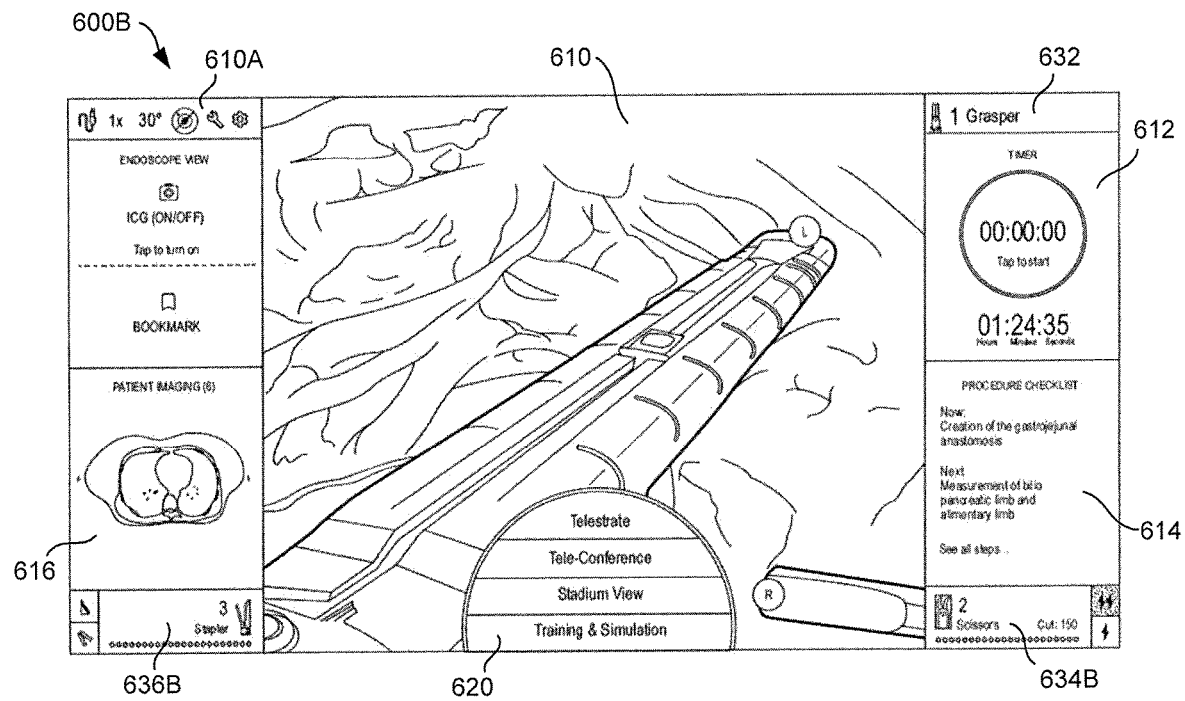
FIG. 6B is a screenshot illustrating another exemplary variation of a GUI with sidebar panels, in accordance with aspects of the subject technology.

FIG. 6A and FIG. 6B depict exemplary GUI variations 600A and 600B in which a video feed portion 610 of the real-time video app is displayed in a main panel between two sidebars on the display. Various apps can be displayed in the sidebars on either side of the main panel, where at least some of the sidebar panels may be selectively hidden, minimized, made transparent, and/or pinned depending on the user's current preference. For example, in FIG. 6A, a stadium view app 611, a timer app 612, a teleconferencing app 613, a procedure template/checklist app 614, a generator app 615, and an image viewer app 616, are displayed on the sidebars of the display. Similarly, in FIG. 6B, a control portion 610a of the real-time video app, the timer app 612, the procedure template/checklist app 614, and the image viewer app 616 are arranged in various subpanels on sidebars around the main panel. Apps populating the sidebar panels may be depicted in a minimalistic style (e.g., simple and clean lines, etc.) or other suitable style. In addition or alternatively, the GUI may be configured to display specialized content from one or more selected software apps in the main panel.

Other apps not depicted in the figures include a patient vitals app, a telestration app, a video labeling app, a video player app, a simulator app, an ergonomic setting app, among other variations of apps. A user may access and activate an app from a tool bar or a quick access menu, (e.g., a quick access menu 620 in FIG. 6B), via an input device or interaction with other suitable sensors. Apps may be represented by graphical icons and/or titles in the tool bar or the quick access ring, and may be arranged in any suitable order, such as grouped by relevance or functionality (e.g., relating to the surgical procedure, relating to the patient, relating to team collaboration), alphabetically, user-selected "favorites," most popular, etc. A user may also customize the form factor of the tool bar or the quick access menu (e.g., circular or ring-shaped, rectangular or other grid of selectable icons or descriptors, drop-down list, or any suitable format). The tool bar or the quick access menu may be displayed in any suitable location on the display (e.g., an open display in the user console). Furthermore, the quick access menu may be configured automatically based on previous effective layouts of the quick access menu for certain kinds of surgical procedures, certain kinds of users, etc.

In some variations, the GUI may display a "tool kit" or tool bar including one or more tool widgets showing surgical tool (instrument) status. For example, the tool kit shown in FIG. 6A includes tool widgets 634A and 636A corresponding to a right-hand tool and a left-hand tool, respectively, and is displayed along a bottom edge of the main panel. In other variations, the tool kit may additionally or alternatively be displayed in any suitable location. As shown in FIG. 6B, the tool kit may include tool widgets 632, 634B, and 636B displayed on side bars of the display and corresponding to a first "backup" surgical instrument located off-screen, a second surgical instrument controlled by a right-hand controller, and a third surgical instrument controlled by a left-hand controller, respectively. Specifically, the tool widget 632, corresponding to the first "backup" surgical instrument, is displayed in an upper corner of a side bar, relatively out-of-sight. The tool widgets 634B and 636B, corresponding to controlled second and third surgical instruments, are displayed in lower corners of right and left side bars, respectively.

In some variations, a tool widget may also display an alert or a notification in response to the detection of a trigger event occurring during a workflow. For example, as shown in FIG. 6A, in the event that one or more sensors (e.g., on a tool driver) detects that an instrument is incorrectly loaded, an associated tool widget may display a notification 621 indicating the problem to a user. Additionally, a separate notification 623 may be displayed elsewhere on the display. The separate notification 623 may, for example, include additional (e.g., more detailed) information relating to the trigger event that is not displayed in the tool widget. Other examples of trigger events may include exhaustion of "lives" of an instrument (e.g., out of a predetermined number of fires of a stapler), an instrument jamming, or other instrument malfunction. Any suitable trigger event for prompting an alert of a notification may be defined. In some variations, alerts or notifications may be prioritized for display in order of urgency.

The image viewer app 616 may be in communication with a medical records database or other suitable repository such that the image viewer app 616 may receive medical images relating to the surgical procedure. For example, the image viewer app 616 may receive and display pre-operative images (e.g., X-ray, CT, MRI, ultrasound, etc.) of the patient. Such display of pre-operative images may allow a surgeon and/or other user(s) to easily view pre-operative images before, during, and/or after a surgical procedure and may help the surgical team make better, more informed decisions relating to the surgical procedure. For example, pre-operative images may be displayed via the image viewer app 616 in order to facilitate pre-operative planning, such as the surgical team reviewing a surgical plan at the outset of a case. As another example, pre-operative images may be displayed via the image viewer app 616 side-by-side with real-time, intra-operative images obtained with an endoscopic (e.g., to assess margins of a tumor to be excised).

The real-time video app is configured to receive and display one or more real-time image data from devices capturing images of a surgical worksite during a surgical procedure. In some variations, the real-time video app is configured to receive and display information in addition to an endoscopic video feed from the robotic surgical system, such as through additional (e.g., third-party) endoscopic devices, ultrasound machines, etc. Display of additional real-time data streams to a user may, for example, help enable surgical staff to view more information (e.g., from different angles or perspectives, with different imaging aids such as ICG or other imaging agents, etc.) that may help them make better treatment decisions. In some variations, the real-time video app may additionally or alternatively receive image data from an endoscopic video feed from the robotic surgical system.

The patient vitals app may be in communication with one or more sensors tracking patient vital signs (or in communication with a memory device storing the same) such as pulse, blood pressure, oximetry data, respiratory rate, temperature, and the like. The display of patient vitals on the display may provide a surgeon and/or other user with easy access to a status of the patient (e.g., without having to ask a present anesthesiologist). The display of patient vital signs in the patient vitals app may, for example, help enable a surgeon react more quickly to emergency situations. Furthermore, the patient vitals app may provide a visual and/or audio alert for trigger events, such as a patient vital meeting a predetermined threshold value (e.g., heart rate exceeding a predetermined value).

The procedure template app 614 may be in communication with a procedure database stored in memory, such that it may receive data relating to procedure planning. The procedure template app 614 may generate a list of items relating to performance of a surgical procedure. For example, the procedure template app 614 may display a checklist of surgical tasks that are part of a surgical procedure, list of equipment or tools needed for the surgical procedure, list of operating room setup tasks, a schematic diagram of port location and arm/surgical instrument setup, etc. In some variations, a checklist may be a template list or may be customized (e.g., a template checklist that has been fine-tuned or adjusted for a particular patient, or an otherwise customized list). The procedure template app 614 may, for example, provide a way for the surgical team to view procedure steps, equipment, and/or setup tasks before or at the outset of a surgical procedure.

The timer app 612 may, for example, track duration of the surgical procedure and/or duration of segments of the surgical procedure (e.g., individual surgical tasks and other tasks performed, and/or groups thereof). In some variations, the timer app 612 may provide a way for medical staff to easily monitor progress of the surgical procedure intraoperatively. Additionally or alternatively, the timer app 612 may analyze (or facilitate analysis of) performance of the surgical procedure post-operatively to help enable the surgical team to identify possible ways to improve efficiency, communication, etc. In some variations, data gathered via the timer app 612 may be displayed on other displays (e.g., additional displays in the operating room) and/or communicated and stored for later analysis. For example, data gathered via the timer app 612 may be uploaded to a web portal or database to help enable an intra-operative and/or post-operative review of the surgical procedure.

The stadium view app 611 provides a real-time view of the robotic system, patient table or bed, and/or staff in an operating room during a procedure. The stadium view app 611 may, in some variations, receive real-time or near real-time information relating to a current position of the robotic arms, patient table, and/or staff and the like, generate a rendering (graphical representation) of the operating room environment based on the received information, and display the rendering to the user. In some variations, the rendering may be in 3D, but may alternatively be in 2D. Alternatively, the rendering may be generated by a remote device (e.g., a separate processor) and passed to the stadium view app 611 for display. Accordingly, the displayed rendering may provide the user with an "outside-the-patient-body" view of the robotic surgical system, the patient, and/or staff, etc. in the operating room. The user may, for example, monitor status of the robotic system such as tool status, potential collisions, etc., and communicate to other members of the surgical team about such status and resolution of any issue.

The teleconferencing app 613 may enable a user to contact a colleague or other contact before, during, and/or after a surgical procedure. For example, the teleconferencing app 613 may enable communication over a cellular network, a wired or wireless internet network (e.g., over WiFi), a direct line network connection, or in any suitable manner. In some variations, the teleconferencing app 613 may store contact information including but not limited to name, picture, role or title, location, phone number or other contact, and the like. Through the teleconference app 613, a user may, for example, seek consultation with a contact for advice or other telementoring, or seek any other suitable kind of collaboration for a surgical procedure. The teleconferencing app 613 may facilitate audio and/or visual collaboration, such as with telephone and/or video conferencing, and/or screen sharing.

The telestration app may enable one or more users to annotate a displayed image or other aspect of the GUI. For example, a telestration app may display a palette of one or more annotation tools. The annotation tools may be used to mark up or label a displayed image such as an endoscopic image, and the annotated image may then be shared between collaborators (e.g., among different GUIs simultaneously displayed on different displays), saved for reference or future analysis, etc. For example, an annotated image may be used to more clearly communicate with a collaborator the location of lesion margins, nearby lymph nodes, and/or other critical anatomical structures (e.g., anatomical targets, tissue to avoid), etc. Collaborators may be among the same surgical team or in the same operating room, and/or may be external to the operating room (e.g., remote collaborators, such as a teleconferencing mentor).

In some variations, a video recording of a surgical procedure may be obtained, such as throughout a surgical procedure. The video labeling app may include annotation tools (e.g., similar to those described above for the telestration app) that may be used to annotate or otherwise label the recorded surgical procedure videos. For example, the video labeling app may help enable users to associate a surgical procedure video with a particular patient (e.g., annotate with patient name, medical record number, etc.), in order to enable future access to the video such as for post-operative review.

The video player app may, for example, be in communication with a video database such that the video player app may receive a video (or a pointer to a video) and display it on the GUI. The video player app may display, for example, an instructional or training video for a relevant surgical procedure or surgical task, or for other tasks relating to the surgical procedure (e.g., setup of ports for docking the robotic arms). In some variations, the video player app may be used by users to review videos in a pre-operative setting, such as to prepare for a surgical procedure. Additionally or alternatively, the video player app may be used to review videos in an intra-operative setting, such as to help resolve a complication that has arisen during the surgical procedure. However, other suitable videos may be played. Furthermore, it should be understood that variants of a video player app (e.g., a music player) may be provided via the GUI.

The generator app 615 may enable control of one or more settings of a surgical instrument. For example, a GUI including a generator app 615 at a user console may enable a surgeon sitting at the user console to control settings of a surgical instrument directly. In some situations, this may increase overall efficiency of the surgical procedure, as a surgeon at the user console may avoid having to ask another member of the surgical staff to change settings.

Control Tower

Figure 7:
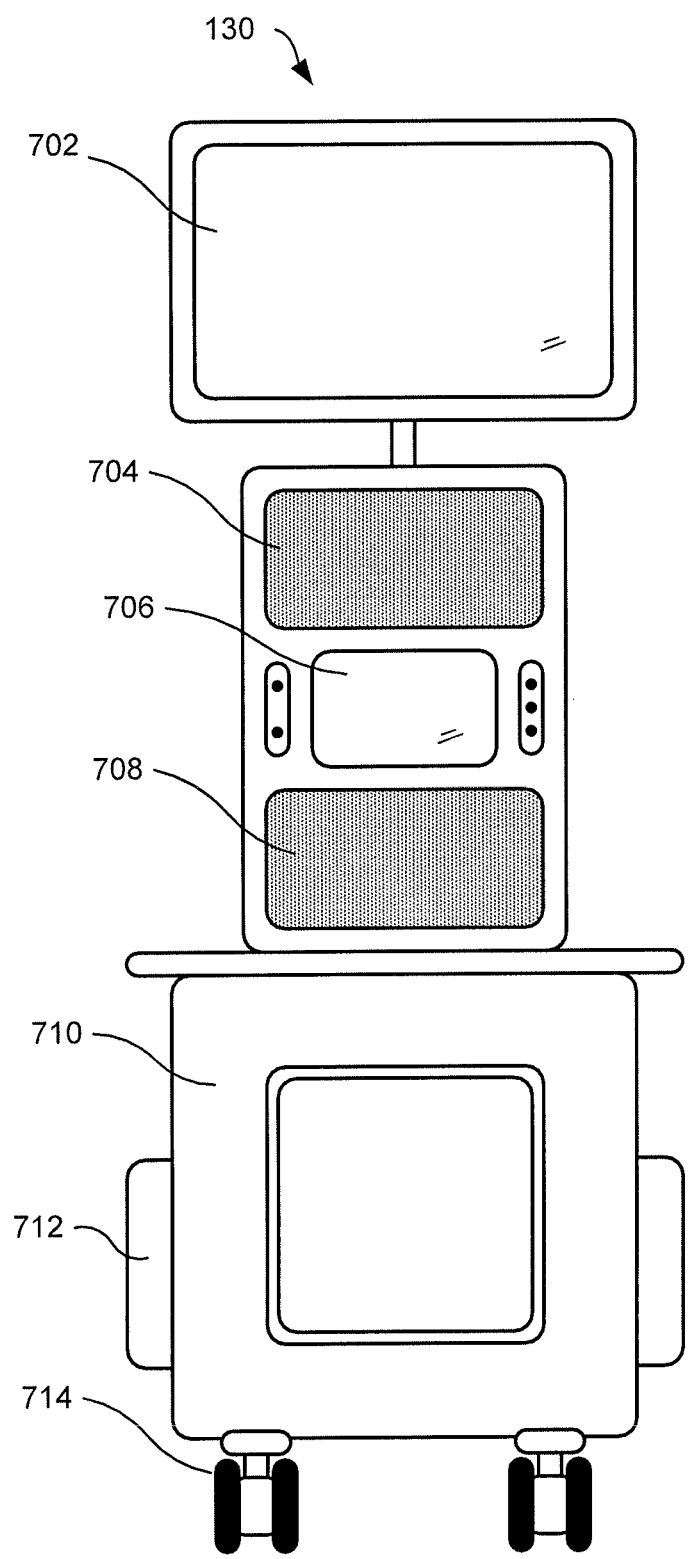
FIG. 7 is a schematic diagram illustrating an exemplary control tower of a surgical robotic system, in accordance with aspects of the subject technology.

FIG. 7 is a schematic diagram illustrating an exemplary control tower 130 for the surgical robotic system, in accordance with aspects of the subject technology. The control tower 130 may house a team display 702, a nurse display 706, accessory shelves 704 and 708, central computers 710 including at least a visualization computer, a control computer and an auxiliary computer, a storage space 712 for cable management and $CO_2$ tanks and casters 714. The team display 702 can provide a view of the surgical site from the patient-side and a set of controls for endoscope and video configurations. For example, the team display 702 may duplicate the entire surgical image seen on the user console open display 450, including endoscope video and apps. In addition to providing instrument status indicators (ready vs. not in use), instrument and foot pedal activation status indicators (activation vs. no activation), and endoscope status/horizontal indicators, the team display may also provide additional on-screen icons, off-screen indicators when instrument is out of view, warnings, alerts, system status, menu, setting and options, and other relevant information, as appropriate.

The nurse display 706 may be a smaller display house on the control tower 130 and may be used by surgical staff to interact with the system in addition to the team display 702. The nurse display may show the status of the endoscope, illuminator, and generator, and allow adjustment to the settings of these devices. In addition, the nurse display 706 may allow user login and access to surgical data and software apps. As shown in FIG. 7, above and below the nurse display 706 are two accessory shelves 704 and 708, though other arrangements of the relative locations between the accessory shelves 704, 708 and the nurse display 706 may be possible. In some variations, the two shelves 704, 708 allow for placement of accessory equipment, such as insufflators, an advanced light engine (ALE), and an external, non-integrated electrosurgical unit (ESU). The ESUs may include monopolar, bipolar, advanced bipolar, and ultrasonic modalities. The ALE contains a high-intensity light source to illuminate the surgical site and electronics for initial processing of endoscopic video images. An endoscope cable may be connected directly from the ALE to the endoscope to provide communication and illumination.

The central computers 710 may include a visualization computer, a control computer, and an auxiliary computer. The visualization computer comprises one or more processors mainly for advanced processing of the video image received from the endoscope via the advanced light engine (ALE) and forwarding the processed video to various displays. The visualization computer may support the graphic user interface, touchscreen input at nurse display and team display, apps responsible for real-time and/or low-latency endoscope video or other video inputs to the system, apps responsible for providing the user time- or safety-critical information via a user console or team display, communication channel between visualization computer and the surgical robotic system, communication of the ALE settings information, activation/deactivation of external ESUs, and audio mixing and export of the audio/video for archival.

The control computer receives user input from the user interface devices at the user console as well as status information from the surgical robot (e.g., table, arms, and instruments), and computes the control commands based on the user input and the robot status. The control commands can then be dispatched to the surgical robot to perform robotically assisted surgeries. The control computer may support the robotic control of the surgical robotic system, including teleoperation, translating UID movement into robotic motion, receiving and transmitting real time data and non-real time data, exporting system data for logging and storage, facilitating table control, arm control and tool control, and managing communication channels between all central computers and the surgical robotic system. The auxiliary computer may also record system logs to internal storage, export system data to internal or external components, and function as a backup computer to the visualization computer and the control computer.

Other accessories (not shown in FIG. 7) of the control tower 130 may include speakers and microphones together with volume controls, and/or audio jacks for audio input and output assisting vocal communication between the surgeon at the user console and bedside staff. The control tower may also include an uninterruptible power supply (UPS) that provides power in the absence of mains power. The control tower can be mobile for optimal positioning in the operating room when the casters 714 (electronic and/or manual) are unlocked. When not in transport mode, the wheel locks/braking system is capable of preventing unwanted movements.

System Architecture

Figure 8:
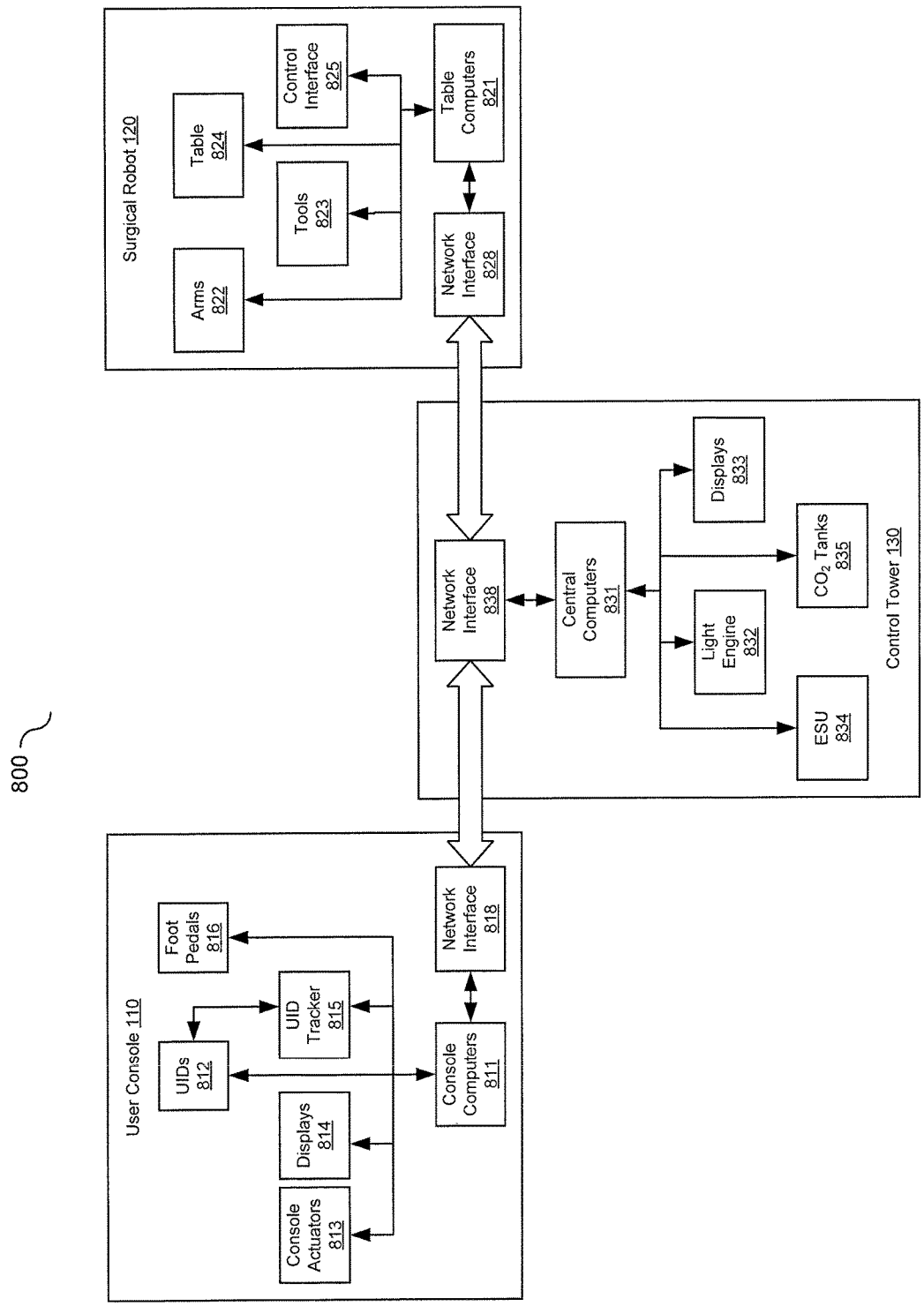
FIG. 8 is a block diagram illustrating exemplary hardware components of a surgical robotic system, in accordance with aspects of the subject technology.

FIG. 8 is a block diagram illustrating an exemplary hardware components of a surgical robotic system 800, in accordance with aspects of the subject technology. The exemplary surgical robotic system 800 may include a user console 110, a surgical robot 120, and a control tower 130. The surgical robotic system 800 may include other or additional hardware components; thus, the diagram is provided by way of example and not a limitation to the system architecture.

As described above, the user console 110 comprises console computers 811, one or more UIDs 812, console actuators 813, displays 814, a UID tracker 815, foot pedals 816, and a network interface 818. A user or surgeon sitting at the user console 110 can adjust ergonomic settings of the user console 110 manually, or the settings can be automatically adjusted according to user profile or preference. The manual and automatic adjustments may be achieved through driving the console actuators 813 based on user input or stored configurations by the console computers 811. The user may perform robot-assisted surgeries by controlling the surgical robot 120 using two master UIDs 812 and foot pedals 816. Positions and orientations of the UIDs 812 are continuously tracked by the UID tracker 815, and status changes are recorded by the console computers 811 as user input and dispatched to the control tower 130 via the network interface 818. Real-time surgical video of patient anatomy, instrumentation, and relevant software apps can be presented to the user on the high resolution 3D displays 814 including open or immersive displays.

Unlike other existing surgical robotic systems, the user console 110 disclosed herein may be communicatively coupled to the control tower 130 over a single fiber optic cable. The user console also provides additional features for improved ergonomics. For example, both an open and immersive display are offered compared to only an immersive display. Furthermore, a highly-adjustable seat for surgeons and master UIDs tracked through electromagnetic or optical trackers are included at the user console 110 for improved ergonomics. To improve safety, eye tracking, head tracking, and/or seat swivel tracking can be implemented to prevent accidental tool motion, for example, by pausing or locking teleoperation when the user's gaze is not engaged in the surgical site on the open display for over a predetermined period of time.

The control tower 130 can be a mobile point-of-care cart housing touchscreen displays, computers that control the surgeon's robotically-assisted manipulation of instruments, safety systems, graphical user interface (GUI), light source, and video and graphics computers. As shown in FIG. 8, the control tower 130 may comprise central computers 831 including at least a visualization computer, a control computer, and an auxiliary computer, various displays 833 including a team display and a nurse display, and a network interface 838 coupling the control tower 130 to both the user console 110 and the surgical robot 120. The control tower 130 may also house third-party devices, such as an advanced light engine 832, an electrosurgical generator unit (ESU) 834, and insufflator and $CO_2$ tanks 835. The control tower 130 may offer additional features for user convenience, such as the nurse display touchscreen, soft power and E-hold buttons, user-facing USB for video and still images, and electronic caster control interface. The auxiliary computer may also run a real-time Linux, providing logging/monitoring and interacting with cloud-based web services.

The surgical robot 120 comprises an articulated operating table 824 with a plurality of integrated arms 822 that can be positioned over the target patient anatomy. A suite of compatible tools 823 can be attached to or detached from the distal ends of the arms 822, enabling the surgeon to perform various surgical procedures. The surgical robot 120 may also comprise control interface 825 for manual control of the arms 822, table 824, and tools 823. The control interface can include items such as, but not limited to, remote controls, buttons, panels, and touchscreens. Other accessories such as trocars (sleeves, seal cartridge, and obturators) and drapes may also be needed to perform procedures with the system. In some variations, the plurality of the arms 822 includes four arms mounted on both sides of the operating table 824, with two arms on each side. For certain surgical procedures, an arm mounted on one side of the table can be positioned on the other side of the table by stretching out and crossing over under the table and arms mounted on the other side, resulting in a total of three arms positioned on the same side of the table 824. The surgical tool can also comprise table computers 821 and a network interface 828, which can place the surgical robot 120 in communication with the control tower 130.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications. They thereby enable others skilled in the art to best utilize the invention and various embodiments with various modifications as are suited to the particular use contemplated. It is intended that the following claims and their equivalents define the scope of the invention.

The methods, devices, processing, and logic described above may be implemented in many different ways and in many different combinations of hardware and software. The controllers and estimators may comprise electronic circuitry.

For example, all or parts of the implementations may be circuitry that includes an instruction processor, such as a Central Processing Unit (CPU), microcontroller, or a microprocessor; an Application Specific Integrated Circuit (ASIC), Programmable Logic Device (PLD), or Field Programmable Gate Array (FPGA); or circuitry that includes discrete logic or other circuit components, including analog circuit components, digital circuit components or both; or any combination thereof. The circuitry may include discrete interconnected hardware components and/or may be combined on a single integrated circuit die, distributed among multiple integrated circuit dies, or implemented in a Multiple Chip Module (MCM) of multiple integrated circuit dies in a common package, as examples.

The circuitry may further include or access instructions for execution by the circuitry. The instructions may be stored in a tangible storage medium that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HDD), or other magnetic or optical disk; or in or on another machine-readable medium. A product, such as a computer program product, may include a storage medium and instructions stored in or on the medium, and the instructions when executed by the circuitry in a device may cause the device to implement any of the processing described above or illustrated in the drawings.

The implementations may be distributed as circuitry among multiple system components, such as among multiple processors and memories, optionally including multiple distributed processing systems. Parameters, databases, and other data structures may be separately stored and managed, may be incorporated into a single memory or database, may be logically and physically organized in many different ways, and may be implemented in many different ways, including as data structures such as linked lists, hash tables, arrays, records, objects, or implicit storage mechanisms. Programs may be parts (e.g., subroutines) of a single program, separate programs, distributed across several memories and processors, or implemented in many different ways, such as in a library, such as a shared library (e.g., a Dynamic Link Library (DLL)). The DLL, for example, may store instructions that perform any of the processing described above or illustrated in the drawings, when executed by the circuitry.

Also, the various controllers discussed herein can take the form of processing circuitry, a microprocessor or processor, and a computer-readable medium that stores computer-readable program code (e.g., firmware) executable by the (micro)processor, logic gates, switches, an application specific integrated circuit (ASIC), a programmable logic controller, and an embedded microcontroller, for example. The controller can be configured with hardware and/or firmware to perform the various functions described below and shown in the flow diagrams. Also, some of the components shown as being internal to the controller can also be stored external to the controller, and other components can be used.

The invention claimed is:

1. A method of operating a control computer in communication with a plurality of robotic surgical instruments, the method comprising:
   receiving user input from one or more input devices at a user console as a user manipulates the one or more input devices;
   generating control commands for the plurality of robotic surgical instruments to follow the user input;
   adjusting, at an open display, at least one endoscopic image of a surgical site to the user according to a gaze point of the user; and
   pause or lock at least one of the robotic surgical instruments when the gaze point of the user deviates for a predetermined time period.

2. The method of claim 1, wherein the open display is adjustable via horizontal translation.

3. The method of claim 1, further comprising:
   detecting a strain of the user; and
   adjusting a seat assembly in response to the detect strain of the user.

4. The method of claim 1, further comprising:
   detecting the gaze point of the user with an eye tracking sensor.

5. The method of claim 2, further comprising:
   projecting a pattern of light on eyes of the user; and
   analyzing reflection of the pattern of light to determine the gaze point of the user.

6. The method of claim 1, further comprising:
   providing, to the open display, an application adjacent to the at least one endoscopic image of the surgical site.

7. The method of claim 6, wherein the application is a patient vitals application configured to display sensor data.

8. The method of claim 6, wherein the application is an image viewer application configured to display pre-operative images for a surgical procedure.

9. The method of claim 6, wherein the application is a procedure template application configured to display a checklist for a surgical procedure.

10. The method of claim 6, wherein the application is a system view application configured to provide a real time view of robotic arms for the plurality of robotic surgical instruments.

11. The method of claim 6, wherein the application is a telestration application configured to receive annotations from the user for at least one endoscopic image of the surgical site.

12. A method of operating a control computer in communication with a robotic surgical instrument, the method comprising:
   receiving user input from one or more input devices at a user console as a user manipulates the one or more input devices;
   generating control commands for the robotic surgical instrument to follow the user input;
   adjusting, at an open display, at least one endoscopic image of a surgical site to the user according to a gaze point of the user; and
   disabling the robotic surgical instrument when the gaze point of the user deviates for a predetermined time period.

13. The method of claim 12, wherein the open display is adjustable via horizontal translation.

14. The method of claim 12, further comprising:
   detecting a strain of the user; and
   adjusting a seat assembly in response to the detect strain of the user.

15. The method of claim 12, further comprising:
   detecting the gaze point of the user with an eye tracking sensor.

16. The method of claim 12, further comprising:
   projecting a pattern of light on eyes of the user; and
   analyzing reflection of the pattern of light to determine the gaze point of the user.

17. The method of claim 12, further comprising:
providing, to the open display, at least one application adjacent to the at least one endoscopic image of the surgical site.

18. The method of claim 17, wherein the at least one application includes two or more of the following:
a patient vitals application configured to display sensor data, an image viewer application configured to display pre-operative images for a surgical procedure,
a procedure template application configured to display a checklist for the surgical procedure,
a system view application configured to provide a real time view of a robotic arm for the robotic surgical instrument, and
a telestration application configured to receive annotations from the user for at least one endoscopic image of the surgical site.

19. A surgical robotic system, comprising:
a user console having one or more input devices and a sensor for tracking a gaze point of a user; and
a control computer communicatively coupled to the one or more input devices and the plurality of robotic surgical instruments, wherein the control computer is configured to:
receive user input from the one or more input devices at a user console as a user manipulates the one or more input devices;
generate control commands for the robotic surgical instrument to follow the user input;
adjust, at an open display, at least one endoscopic image of a surgical site to the user according to a gaze point of the user; and
disable the robotic surgical instrument when the gaze point of the user deviates for a predetermined time period.

20. The surgical robot system of claim 19, wherein the open display is adjustable via horizontal translation.

* * * * *